United States Patent [19]

Harnisch

[11] 4,370,486
[45] Jan. 25, 1983

[54] BIPHENYL COMPOUNDS, A PROCESS FOR THEIR PREPARATION AND THEIR USE AS INTERMEDIATE PRODUCTS FOR OPTICAL BRIGHTENERS, DYESTUFFS, PLASTICS AND MEDICAMENTS

[75] Inventor: Horst Harnisch, Much, Fed. Rep. of Germany

[73] Assignee: Bayer Aktiengesellschaft, Leverkusen, Fed. Rep. of Germany

[21] Appl. No.: 292,868

[22] Filed: Aug. 14, 1981

[30] Foreign Application Priority Data

Sep. 2, 1980 [DE] Fed. Rep. of Germany ....... 3033002
Dec. 19, 1980 [DE] Fed. Rep. of Germany ....... 3048088

[51] Int. Cl.³ .................. C07C 103/38; C07C 103/76
[52] U.S. Cl. .................................. 549/46; 260/465 D; 260/507 R; 548/455; 548/477; 548/479; 564/155; 564/158; 564/166; 564/176; 564/185; 564/212
[58] Field of Search ............ 260/326 D, 326 S, 326 N, 260/465 D, 507 R; 549/46; 564/155, 158, 166, 176, 185, 212

[56] References Cited

U.S. PATENT DOCUMENTS 4,041,056 8/1977 Heintzelmann et al. ......... 260/404.5

FOREIGN PATENT DOCUMENTS 499134 1/1954 Canada .
836194 4/1952 Fed. Rep. of Germany .
2810085 9/1979 Fed. Rep. of Germany .
3003539 8/1981 Fed. Rep. of Germany .

Primary Examiner—Richard Raymond
Attorney, Agent, or Firm—Sprung, Horn, Kramer & Woods

[57] ABSTRACT

Biphenyl compounds of the formula

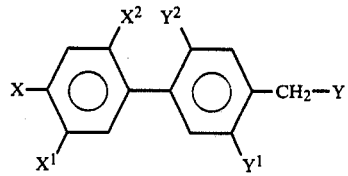

in which
the substituents have the meanings given in the description, are obtained by amidomethylation of the corresponding starting compounds and, if appropriate, subsequent sulphonation. The new compounds are used, for example, for the preparation of dyestuff precursors, dyestuffs, plastics and medicaments.

3 Claims, No Drawings

BIPHENYL COMPOUNDS, A PROCESS FOR THEIR PREPARATION AND THEIR USE AS INTERMEDIATE PRODUCTS FOR OPTICAL BRIGHTENERS, DYESTUFFS, PLASTICS AND MEDICAMENTS

The invention relates to compounds of the general formula

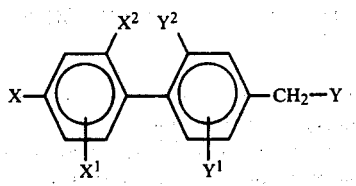

wherein
X represents hydrogen, —CH$_2$—Y, SO$_3$H or a radical A,
A represents C$_1$–C$_6$-alkyl, trifluoromethyl, cyclohexyl, C$_1$–C$_4$-alkoxy, chlorine, bromine or fluorine,
X$^1$ represents hydrogen, methyl, chlorine or SO$_3$H,
X$^2$ represents hydrogen or methyl,
Y represents an acetamido or propionylamido radical which is substituted in the α-position by 1 to 3 halogen atoms, or an optionally substituted benzamido group or a phthalimido group,
Y$^1$ represents hydrogen, methyl or SO$_3$H and
Y$^2$ represents hydrogen, or
X$^2$ and Y$^2$ together form an ethylene radical or a —SO$_2$— bridge, with the proviso that at least one radical Y represents halogen-substituted acetamido or propionylamido or optionally substituted benzamido if the compounds are free from sulphonic acid groups or from —SO$_2$—bridges.

The maximum total number of sulphonic acid groups is preferably 2. By "halogen" there is to be understood chlorine, bromine and fluorine, in particular chlorine.

Suitable C$_1$–C$_6$-alkyl radicals A are, for example, methyl, ethyl, isopropyl, tertiary butyl, n-butyl, isoamyl and n-hexyl. C$_1$–C$_4$-alkyl radicals are preferred.

Suitable C$_1$–C$_4$-alkoxy groups are, preferably, methoxy, ethoxy, isopropoxy, n-butoxy, tertiary butoxy, β-methoxy-ethoxy and β-ethoxy-ethoxy.

Examples of Y which may be mentioned are: chloroacetamido, dichloroacetamido, trichloroacetamido, trifluoroacetamido, bromoacetamido, benzamido and phthalimido; preferred radicals are chloroacetamido, dichloroacetamido and trichloroacetamido, in particular chloroacetamido, and benzamido.

Benzamido radicals Y can contain up to 3 substituents on the nucleus, in particular C$_1$–C$_4$-alkyl, such as methyl, ethyl, isopropyl and tertiary butyl; halogen, such as chlorine and bromine; C$_1$–C$_2$-alkoxy, such as methoxy and ethoxy; and nitro and cyano. The amide nitrogen atom can also be substituted by a C$_1$–C$_2$-alkyl group.

Suitable substituted benzamido radicals Y are, for example, 4-methyl-, 2-methyl-, 2,4-dimethyl-, 2,4,6-trimethyl-, 4-isopropyl-, 4-tert.-butyl-, 4-chloro-, 2-chloro-, 2,4-dichloro-, 3-bromo-, 4-methoxy-, 4-ethoxy-, 3-nitro-, 4-cyano-, N-methyl- and N-ethyl-benzamido. In addition to the unsubstituted benzamido, the 4-methyl and 4-chlorine derivatives are most important from an industrial point of view.

In the context of the invention, a preferred group of compounds corresponds to the formula

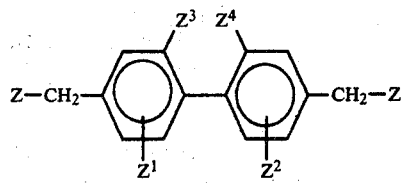

wherein
Z represents chloroacetamido, dichloroacetamido, trichloroacetamido or benzamido,
Z$^1$ and Z$^2$ independently of one another represent hydrogen or SO$_3$H and
Z$^3$ and Z$^4$ individually represent hydrogen or together represent ethylene or a —SO$_2$— bridge. A further preferred group of compounds of the formula (I) corresponds to the formula

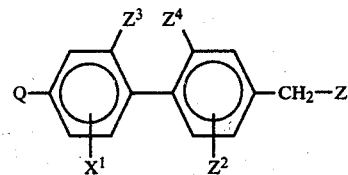

wherein
Z, Z$^2$, Z$^3$ and Z$^4$ have the same meaning as in formula (II),
X$^1$ has the same meaning as in formula (I) and
Q represents hydrogen, C$_1$–C$_4$-alkyl, cyclohexyl, C$_1$–C$_2$-alkoxy, chlorine, bromine or SO$_3$H, with the proviso that at most one of the radicals Q and X$^1$ denotes SO$_3$H.

Those compounds of the formula (II) or (III) in which Z$^3$ and Z$^4$ represent hydrogen and Z represents chloroacetamido or benzamido are of particular industrial value.

An advantageous process for the preparation of compounds of the formula (I) is characterised in that compounds of the general formula

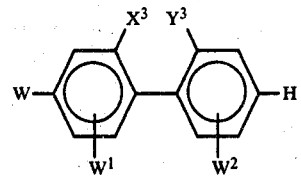

wherein
W represents hydrogen or a radical A,
W$^1$ represents hydrogen, methyl or chlorine,
W$^2$ and X$^3$ each by itself represents hydrogen or methyl and
Y$^3$ represents hydrogen, or
X$^3$ and Y$^3$ together represent ethylene, and
A has the abovementioned meaning, are subjected to a condensation reaction with one or—in the case where W=H—if desired also with two equivalents of a compound of the formula $$Y-CH_2-OH \quad (V)$$

wherein

Y has the same meaning as in formula (I), water being split off, and, if appropriate, the product is then reacted with a sulphonating agent.

The amidomethylation of (IV) with (V) corresponds to a reaction of the Tscherniak-Einhorn type (Houben-Weyl XI/1 (1957), 795; Org. Reactions 14 (1965), 52 and Synthesis 1970, 49).

Mixtures of sulphuric acid and one or more lower fatty acids, such as acetic acid and propionic acid, serve as the reaction medium. The reaction is carried out in the temperature range from −10° to +50° C., preferably at 0°-25° C.

It is to be described as decidedly surprising that the amidomethylation products of the formula I are obtained in a high yield and good purity under these reaction conditions, since under standard conditions, that is to say in concentrated sulphuric acid, this reaction does not proceed particularly selectively and thus leads to products which cannot be used industrially. It is also surprising that other marketable methylol components than those of the formula I, such as, for example, methylolformamide or methylolacetamide, do not react so smoothly.

The starting compounds of the formulae (IV) and (V) are known, or they are accessible by known methods.

Instead of the methylol compounds of the formula (V), mixtures of the corresponding amides Y-H with at least the equivalent amount of formaldehyde, preferably paraformaldehyde, can also advantageously be employed. In another process variant, it is also possible to employ, instead of primary amides Y-H, the corresponding nitriles, such as chloro-, dichloro-, trichloro- or trifluoro-acetonitrile or benzonitrile.

By the procedure described above, it is also possible to obtain 4,4'-bis-(phthalimidomethyl)-biphenyl, which could hitherto be obtained only in a yield of 49% of theory by the method described in Ukr. Khim. Zh. 26, 277 (1960), in a substantially higher yield (93% of theory) and purity from biphenyl and two equivalents of hydroxymethylphthalimide.

Representatives of the formula (I) which contain sulphonic acid groups and/or —SO$_2$— bridges are prepared, after the amidomethylation, by reaction with a sulphonating agent, such as sulphuric acid (containing 0-65% of free SO$_3$), chlorosulphonic acid, pyridine-N-sulphonic acid or SO$_3$, it being possible, as a rule, for the sulphonating agent simultaneously to serve as the reaction medium. The reaction is carried out in the temperature range from −10° to 130° C., and generally preferably at 0°-30° C., or preferably at 60°-120° C. in the case of compounds containing —SO$_2$— bridges.

Amidomethyl compounds (I) which are unsubstituted in the 3-position and are free from SO$_3$H groups and —SO$_2$— bridges as a rule react smoothly in 100% strength sulphuric acid to give the corresponding monosulphonic acid. In contrast, surprisingly, the same compounds give the sulphone (X$^2$+Y$^2$=—SO$_2$—) in 20% strength oleum.

The compounds of the formula (I) are valuable new intermediate products for the preparation of optical brighteners, dyestuffs and plastics which have a high industrial value.

The first step taken to obtain optical brighteners or plastics from the new intermediate products of the formula (I) can comprise hydrolysis of these intermediate products to give the corresponding aminomethyl compounds of the formula

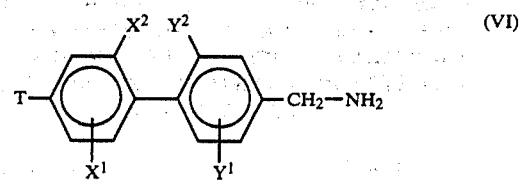

wherein

T represents hydrogen, —CH$_2$NH$_2$, SO$_3$H or a radical A, wherein

A and the remaining radicals have the same meaning as in formula (I), or to give inner or acid salts of these aminomethyl compounds, such as, for example, hydrochlorides, hydrobromides, hydrosulphates or hyperchlorates. The hydrolysis can be carried out under customary conditions by heating with aqueous mineral acids, such as hydrochloric acid, hydrobromic acid, sulphuric acid or phosphoric acid, or with aqueous alkali metal hydroxide, such as sodium hydroxide solution or potassium hydroxide solution, to temperatures of 30°-200° C., preferably 80°-160° C., advantageously in the presence of a water-miscible inert organic solvent, such as ethylene glycol or—in the case of acid hydrolysis—also glacial acetic acid or propionic acid.

Phthalimidomethyl compounds can also easily be split into the corresponding aminomethyl compounds of the formula (VI) with hydrazine.

Compounds of the formula (VI) which contain —SO$_2$— bridges or sulphonic acid groups can also be prepared from the compounds which are free from —SO$_2$— bridges or sulphonic acid groups by subsequent reaction with a sulphonating agent, the above-mentioned sulphonating agents being used and the abovementioned reaction conditions being applied. Preferred representatives of compounds of the formula (VI) which contain —SO$_2$— bridges correspond to the formula

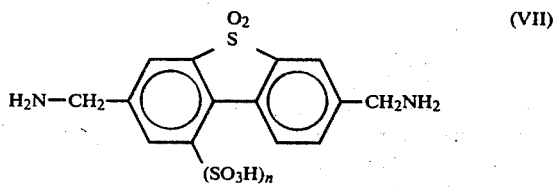

wherein n represents the number 0 or 1.

Preferred representatives of compounds of the formula VI which are free from —SO$_2$— bridges but contain sulphonic acid groups correspond to the formula

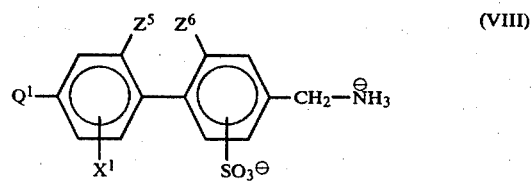

wherein

X$^1$ represents hydrogen, methyl, chlorine or SO$_3$H,

Q$^1$ represents hydrogen, C$_1$-C$_4$-alkyl, C$_1\oplus$-C$_2\ominus$-alkoxy, chlorine, bromine, SO$_3$H or CH$_2$-NH$_3$An, An⊖ represents an anion and $Z^5$ and $Z^6$ individually represent hydrogen or together represent ethylene, with the proviso that at most one of the radicals $Q^1$ and $X^1$ denotes SO$_3$H.

By anions An⊖ there are understood the equivalents of customary acid anions, such as chlorides, sulphates, bisulphates, nitrates, phosphates, hydrogen phosphates, perchlorates, chlorozincates and acetates. An⊖ can, however, also be represented by a SO$_3$⊖ group $Q^1$ or $X^1$ present in the same molecule.

Whilst all the compounds of the formula (VI) can advantageously be used for the synthesis of optical brighteners, more specific types are employed in other fields.

Bifunctional compounds of the formula (VI) which are free from sulpho groups and in which T represents —CH$_2$—NH$_2$ are valuable components for polyamides (U.S. Pat. No. 4,041,056) and for antiphlogistic and antipyretic agents (U.S. Pat. No. 3,646,782). Monofunctional compounds of the formula (VI) which are free from sulpho groups and in which T is C$_1$-C$_4$-alkoxy are immediate precursors of compounds which lower the levels of cholesterol and triglycerides (German Offenlegungsschrift No. 2,500,692).

In order to obtain optical brighteners, the aminomethyl compounds of the formula VI are reacted, for example, with nitrous acid or with a C$_1$-C$_5$-alkyl ester thereof and a mineral acid in a further stage in a manner which is known per se (Houben-Weyl XI/2 (1958), 133-137), N$_2$ being split off, to give the corresponding hydroxymethyl compounds of the formula

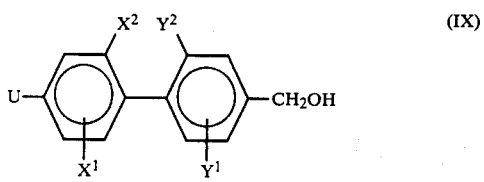

(IX)

wherein

U represents hydrogen, —CH$_2$OH, SO$_3$H or a radical A, wherein A and the remaining radicals have the same meaning as in formula (I), and thereafter, these compounds are either oxidised under mild conditions in a manner which is known per se (Houben-Weyl, VII/1 (1954) 177; and Synthesis 1976, 88-89) to give the aldehydes of the formula

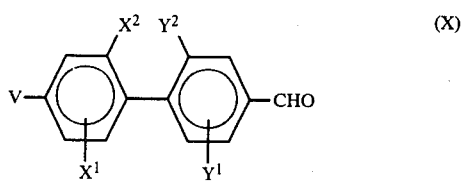

(X)

wherein

V represents hydrogen, -CHO, SO$_3$H or a radical A, wherein A and the remaining radicals have the same meaning as in formula (I), or these compounds are reacted with hydrogen chloride or inorganic acid chlorides, such as thionyl chloride phosphorus trichloride or phosphorus pentachloride, in a manner which is known per se (Houben-Weyl, V/3 (1962) 830-837, 812-869, 899 and 905-911) to give the corresponding chloromethyl compounds of the formula

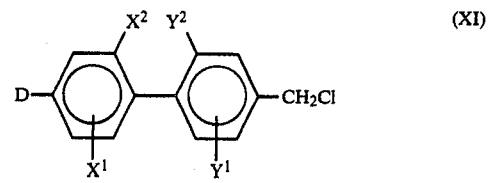

(XI)

wherein

D represents hydrogen, —CH$_2$Cl, SO$_3$H or a radical A, wherein A and the remaining radicals have the same meaning as in formula (I), and wherein sulpho can in each case also be in the form of the acid halide, and these compounds are then reacted with reagents such as trialkyl phosphite, an alkali metal dialkoxyphosphonate or triphenylphosphine to give the corresponding methyl compounds which are activated by phosphorus, these compounds, like the aldehydes of the formula (X), being immediate precursors of optical brighteners and laser dyestuffs which have biphenyl structural elements and conjugated ethylene double bonds (German Auslegeschrift No. 1,794,386, German Offenlegungschrift No. 2,201,857, German Offenlegungsschrift No. 2,209,221, German Offenlegungsschrift No. 2,262,340, German Offenlegungsschrift No. 2,262,531, German Offenlegungsschrift No. 2,262,632, German Offenlegungsschrift No. 262,633, German Offenlegungssschrift No. 2,241,304, German Offenlegungsschrift No. 2,453,357, German Offenlegungsschrift No. 2,337,845, German Offenlegungsschrift No. 2,700,292, German Offenlegungsschrift No. 2,841,519, European Offenlegungsschrift No. 1,991 and U.S. Pat. No. 3,907,904).

Bischloromethyl compounds of the formula (XI) (D=CH$_2$Cl) also give valuable important optical brighteners of the 4,4'-bis-(benzofuran-2-yl)-biphenyl series with two equivalents of salicylaldehyde (German Offenlegungsschrift 2,238,734).

The bischloromethyl compounds required as starting materials have hitherto been accessible on an industrial scale only by chloromethylation of biphenyl, but by-products which can damage health are formed. Handling and removal of these by-products necessitates a considerable expenditure on apparatus.

The process according to the invention does not have these disadvantages.

The aldehydes of the formula (X) can also be prepared from the aminomethyl compounds of the formula (VI) by other advantageous routes, for example by Sommelet oxidation with hexamethylenetetramine in a weakly acid medium (this method is described, for example, in J. Chem. Soc. 1953, 1740-41) or with hydrogen peroxide in the presence of a tungstate (a method which is described in Chem. Ber. 93 (1960) 133 and Houben-Weyl X/4 (1957) 123-124 and which leads to the aldoximes), or by condensation with a carbonyl compound of the formula O=CR$^1$R$^2$, wherein R$^1$ represents hydrogen or C$_1$-C$_8$-alkyl and R$^2$ represents C$_1$-C$_8$-alkyl, or R$^1$ and R$^2$ together represent C$_4$-C$_8$-alkylene, subsequent base-catalysed rearrangement of the —N═C— double bond in conjugation with the aromatic ring and splitting off the resulting azomethine under acid conditions (this method is described in European Offenlegungsschrift 8,323).

Chloromethyl compounds of the formula (XI) can also advantageously be prepared directly from the corresponding aminomethyl compounds of the formula (VI) by reaction with nitrosyl chloride by the method described in Houben-Weyl V/3 (1962) 940.

Chloromethyl compounds of the formula (XI) are prepared in a high yield in a particularly rational manner by a process in which compounds of the formula I in which Y denotes optionally substituted benzamido are reacted with PCl₅ or SOCl₂ by a v. Braun reaction (Chem. Ber. 87 (1904) 2678, 2812, 3210 and 3583; Houben-Weyl V/3 (1962) 921 and JACS 84 (1962) 769). It is expedient to carry out this reaction in an inert organic solvent, such as, for example, chlorobenzene or o-dichlorobenzene, in the temperature range from 60° to 150° C., benzonitrile being split off.

The bromomethyl compounds analogous to the chloromethyl compounds of the formula (II) can be prepared by reacting (IX) with PBr₃, POBr₃ or PBr₅, by the action of NO and bromine on (VI) by the process described in Houben-Weyl V/4 (1960) 455 or by reacting benzamidomethyl compounds (I) with PBr₃ and bromine or PBr₅ by the v. Braun method described in Houben-Weyl V/4 (1960) 451.

Compounds of the formula (I) in which Y represents the chloro- or bromo-acetamido radical can be reacted with an alkali metal cyanide to give new cyanoacetamido compounds of the formula

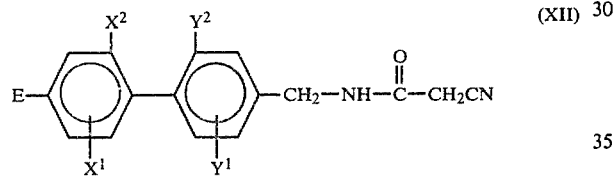
(XII)

wherein

E represents hydrogen, —CH₂—NH—CO—CH₂CN, SO₃H or a radical A, wherein A and the remaining radicals have the same meaning as in formula (I). These are new dyestuff precursors which are capable of undergoing coupling and condensation, of which the 4,4′-bis-cyanoacetamidomethyl derivatives are preferred.

The reaction of I with an alkali metal cyanide is carried out in a polar, water-miscible medium, such as methanol, ethanol, isopropanol, ethylene glycol or ethylene glycol monomethyl ether, preferably in a dipolar aprotic solvent, such as dimethylformamide or dimethylsulphoxide, in the temperature range from 10° to 80° C., preferably at 30°–60° C.

It is moreover worth noting that some of the secondary products described by the formulae VI and X have not yet been described in the literature. However, they are to a great extent suitable as key products for the abovementioned fields of use. Particular examples are those compounds of the formula VI or X which contain a sulpho group and/or a —SO₂— bridge (X²+Y²=—SO₂—). The provision of the biphenyl compounds of the formula I according to the invention and of the preparation process leading to these substances thus opens up rational routes to these important new key products.

Amongst these compounds, those which correspond to the formula

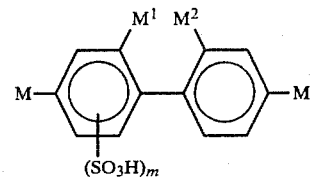
(XIII)

wherein

M represents —CH₂—NH₂ (as a base or an inner or acid salt) or —CH=O,

M¹ and M² individually represent hydrogen or together represent —SO₂— and m represents the number 1 or, in the case where M¹+M²=—SO₂—, also 0, are of particular industrial importance.

Characteristic examples of such secondary products of the formula XIII are:

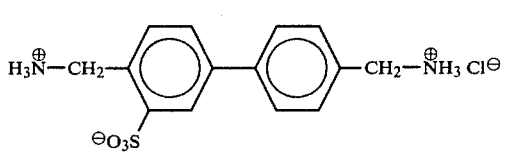
XIV

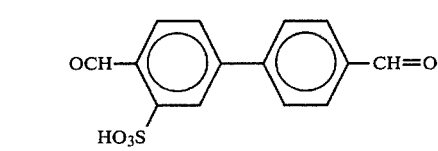
XV

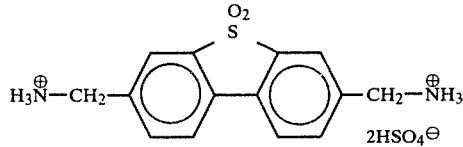
XVI

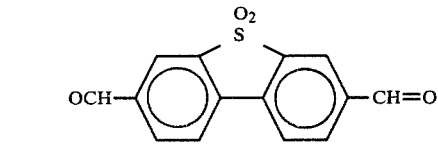
XVII

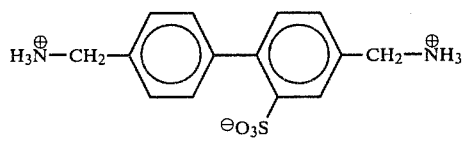
XVIII

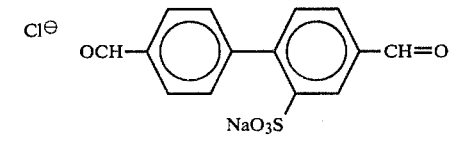
XIX

As already described in detail above, these secondary products are most easily obtained from the biphenyl compounds of the formula I according to the invention (after the reaction with a sulphonating agent) by acid hydrolysis to give the corresponding aminomethyl compounds and, if appropriate, subsequent oxidation with urotropin.

EXAMPLE 1

385 g of biphenyl are dissolved in 1.5 l of propionic acid at 30° C., and 0.9 l of concentrated sulphuric acid is added dropwise at 10°–15° C, with severe cooling. 514 g of chloroacetamide and 233 g of paraformaldehyde are added to the resulting suspension at 10°–15° C. The reaction mixture is stirred at 15° C. for 11 hours and left to stand for a further 20 hours at 15°–18° C. without being stirred. 3 kg of ice are then added and the mixture is stirred at room temperature for 1 hour. The crystalline precipitate is filtered off over an acid-resistant filter, washed neutral with 40 l of water and pressed off well. About 1 kg of the compound of the formula

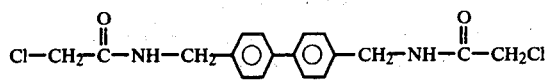

is obtained as a moist presscake, which is advantageously further processed in this form. If desired, the substance can be dried at 50° C. in vacuo. Yield: 820 g of the colourless crystalline powder. A sample recrystallised from glacial acetic acid has a melting point of 222°–224° C., m/e=364 (M⊕, dichloro).

The compounds of the general formula

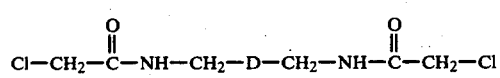

listed in the table which follows are prepared in an analogous manner:

| Example | D | m/e |
|---|---|---|
| (2) | 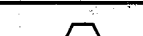 | 390 (M⊕, dichloro) |
| (3) |  | 392 (M⊕, dichloro) |

EXAMPLE 4

38.5 g of biphenyl are dissolved in 150 ml of propionic acid at 35° C., and 90 ml of concentrated sulphuric acid are added dropwise at 10°–15° C., with severe cooling. 70.5 g of dichloroacetamide and 23.3 g of paraformaldehyde are added to the resulting suspension at 10°–15° C. The reaction mixture is stirred at 15° C. for 11 hours and left to stand for a further 20 hours at 15°–18° C. without being stirred. 300 g of ice are then added and the mixture is stirred at room temperature for 1 hour. The crystalline precipitate is filtered off over an acid-resistant filter, washed neutral with 0.5 l of water and pressed off well. After drying at 50° C. in vacuo, 97 g of the compound of the formula

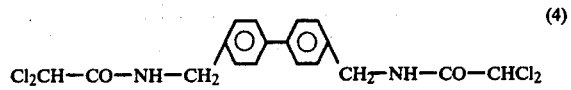

are obtained as a colourless crystalline powder. Melting point: 227°–228° C. (from glacial acetic acid; m/e=432 (M⊕, tetrachloro)).

EXAMPLE 5

If the dichloroacetamide in Example 4 is replaced by an equivalent amount of trichloroacetamide, 114 g of the compound of the formula

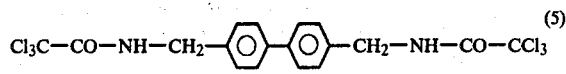

are obtained; m/e=500 (M⊕, hexachloro).

If the dischloroacetamide is replaced by α-chloropropionamide or bromoacetamide, 4,4'-(α-chloropropionylamidomethyl)-biphenyl, m/e=392 (M⊕, dichloro) or 4,4'-(bromoacetamidomethyl)-biphenyl, m/e=454 (M⊕) is obtained analogously.

EXAMPLE 6

308 g of biphenyl are dissolved in 1,750 ml of glacial acetic acid, with warming, and 1,500 ml of concentrated sulphuric acid are added dropwise at 20°–25° C., with severe cooling. 533 g of benzamide and 132 g of paraformaldehyde are then added and the mixture is stirred at room temperature for 20 hours and discharged onto 10 l of ice-water. After stirring the mixture for 2 hours, the crystalline precipitate is filtered off, washed neutral with water and dried at 50° C. in vacuo. 840 g of the compound of the formula

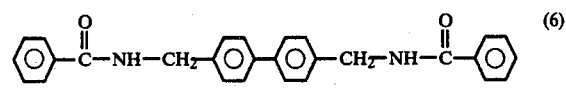

are obtained. Melting point: 247° C. (from glacial acetic acid); m/e=420 (M⊕).

The following compounds of the general formula

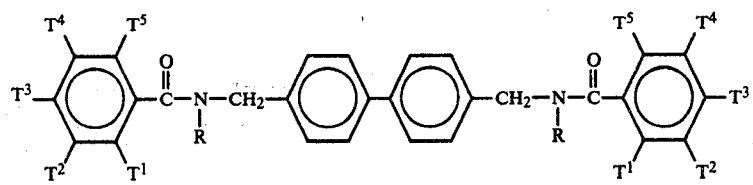

are prepared in an analogous manner:

| Example | R | $T^1$ | $T^2$ | $T^3$ | $T^4$ | $T^5$ | m/e | (M⊕) |
|---|---|---|---|---|---|---|---|---|
| (7) | $CH_3$ | H | H | H | H | H | 448 | |
| (8) | H | H | H | $CH_3$ | H | H | 448 | |
| (9) | H | H | H | Cl | H | H | 488 | (dichloro) |
| (10) | $C_2H_5$ | H | H | H | H | H | 476 | |
| (11) | H | H | H | $(CH_3)_3$ | H | H | 532 | |
| (12) | H | $CH_3$ | H | $CH_3$ | H | $CH_3$ | 504 | |
| (13) | H | H | H | $OCH_3$ | H | H | 480 | |
| (14) | H | H | H | $OC_2H_5$ | H | H | 508 | |

-continued

| Example | R | T¹ | T² | T³ | T⁴ | T⁵ | m/e | (M⊕) |
|---|---|---|---|---|---|---|---|---|
| (15) | H | H | Cl | Cl | H | H | 556 | (tetrachloro) |

EXAMPLE 16

308 g of biphenyl are dissolved in 1,750 ml of glacial acetic acid, with warming, and 1,300 ml of concentrated sulphuric acid are added dropwise at 20°-25° C., with severe cooling. 789 g of N-methylolphthalimide are then added, the mixture is stirred at room temperature for 20 hours and 2.5 l of water are added dropwise, also at room temperature, with severe cooling. After stirring the mixture for 1 hour, the crystalline precipitate is filtered off, washed neutral with water and dried at 80° C. in vacuo. 878 g (93% of theory) of the compound of the formula

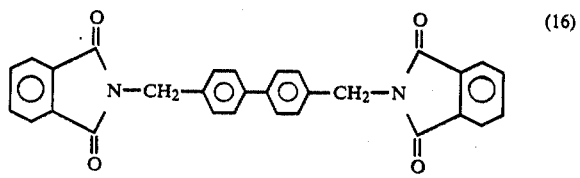

(16)

are obtained. Melting point: 299° C. (from glacial acetic acid); m/e=472 (M⊕).

EXAMPLE 17

38.5 g of biphenyl are dissolved in 220 ml of propionic acid and the solution is cooled to 10° C. 30 ml of concentrated sulphuric acid are added dropwise at 10°-15° C., with severe cooling, and 37.4 g of chloroacetamide and 12 g of paraformaldehye are then added to the solution. After stirring the reaction mixture at 15° C. for 20 hours, it is discharged onto 1 l of ice-water and the crystalline precipitate is filtered off and washed neutral with water. The moist presscake is boiled with 250 ml of toluene, using a water separator, in order to remove the water, whereupon a clear solution is formed. After cooling the solution, the crystalline precipitate is filtered off, washed with petroleum ether and dried at 40° C. in vacuo. 8 g of the compound of the formula (17)

$$\text{biphenyl-CH}_2\text{—NH—}\underset{\underset{O}{\|}}{C}\text{—CH}_2\text{Cl}$$

are obtained. Melting point: 149°-150° C.; m/e=259 (M⊕, monochloro).

After evaporating off the solvent from the toluene mother liquor, 62% of the biphenyl employed is recovered.

EXAMPLE 18

64.5 g of chloroacetamide and 29.5 g of paraformaldehyde are added to 115 g of 4-methoxy-biphenyl in 2.5 l of propionic acid and the mixture is warmed to 85° C., whereupon a clear solution is formed. This solution is cooled to 20° C., 135 ml of concentrated sulphuric acid are added dropwise at 20°-25° C., with severe cooling, and the mixture is stirred at 20°-25° C. for 5 hours and then discharged onto 5 l of ice-water. The crystalline precipitate is filtered off, washed neutral with water and dried at 50° C. in vacuo. 164 g of the compound of the formula (18)

$$\text{CH}_3\text{O—biphenyl—CH}_2\text{NH—}\underset{\underset{O}{\|}}{C}\text{—CH}_2\text{Cl}$$

are obtained. Melting point: 132°-133° C. (from di-sec.-butyl ether); m/e=289 (M⊕, monochloro).

The compounds of the general formula

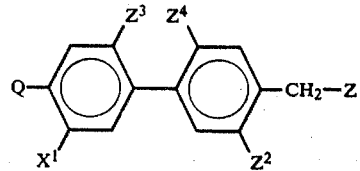

listed in the table which follows are prepared in an analogous manner:

| Example | Q | X¹ | Z² | Z³ | Z⁴ | Z | m/e |
|---|---|---|---|---|---|---|---|
| (19) | CH₃ | H | H | H | H | NH—CO—CH₂Cl | 273 (M⊕) |
| (20) | C(CH₃)₃ | H | H | H | H | NH—CO—CHCl₂ | 349 (M⊕) |
| (21) | ⟨H⟩— | H | H | H | H | NH—CO—CCl₃ | 409 (M⊕) |
| (22) | Br | H | H | H | H | NH—CO—CH₂Cl | 338 (M⊕) |
| (23) | Cl | Cl | H | H | H | NH—CO—⟨○⟩ | 355 (M⊕) |

-continued

| Example | Q | $X^1$ | $Z^2$ | $Z^3$ | $Z^4$ | Z | m/e |
|---|---|---|---|---|---|---|---|
| (24) | Cl | $CH_3$ | H | H | H | 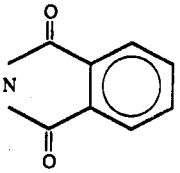 | 361 ($M^\oplus$) |
| (25) | $C_2H_5O$ | H | H | H | H | $NH-COCH_2Cl$ | 303 ($M^\oplus$) |
| (26) | $CH_3$ | $CH_3$ | $CH_3$ | H | H | $NH-COCH_2Cl$ | 301 ($M^\oplus$) |
| (27) | $CH_3$ | H | H | $-CH_2-CH_2-$ | | $NH-CO-CH_2Cl$ | 299 ($M^\oplus$) |

EXAMPLE 28

1/10 of the moist presscake of compound (1) prepared according to Example 1 is suspended in 680 ml of dimethylformamide, the suspension is warmed to 40°-45° C. with 85 ml of 30% strength by volume sodium cyanide solution for 4 hours and the mixture is discharged onto 4 l of ice-water and stirred. The crystalline precipitate is filtered off, washed with water and dried at 80° C. in vacuo.

Yield: 78.5 g of the compound of the formula

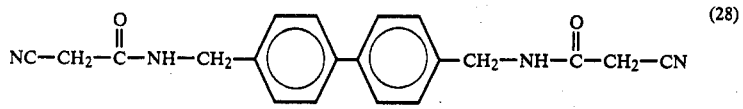

(28)

Melting point: 270°-271° C. (from glacial acetic acid); m/e=346 ($M^\oplus$).

EXAMPLE 29

60 g of the compound of the formula (1) are gradually introduced into 600 g of 100% strength sulphuric acid at 5°-20° C., with stirring and cooling, and the mixture is stirred at 20°-25° C. for 1 day and discharged onto 1 kg of ice. After stirring the mixture for 1 hour, the crystalline precipitate is filtered off, washed with ice-water and dried at 60° C. in vacuo. 81.2 g of the compound of the formula

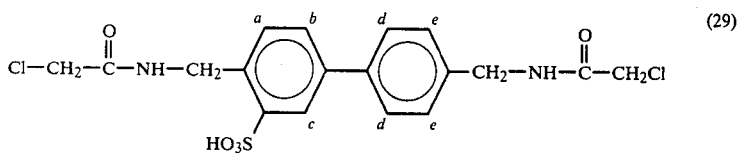

(29)

are obtained. It can be purified by stirring with acetone.

$^1$H-NMR ([$D_6$]-DMSO/TMS): δ=4.12 (S; 4H, $CH_2Cl$), 4.30 (broad d, J=6 Hz; 4H, —$CH_2$—NH—), 7.17 (d, J=8 Hz; 1H, $H_a$), AA'BB'-signal ($δ_A$=7.50, $δ_B$=7.17, $J_1$=8 HZ, $J_2$ not resolved; 4H, $H_a+H_d$), 7.50 (dd, $J_1$=8 Hz, $J_2$ not resolved; 1H, $H_b$), 7.85 (d, J=1.5 Hz; 1H, $H_c$), and 8.76 (t, J=6 Hz; 2H, N$\underline{H}$).

EXAMPLE 30

500 g of the compound of the formula (1) which has been prepared according to Example 1 and has then been extracted by stirring with glacial acetic acid and drying at 80° C. in vacuo are introduced in portions to 2.6 kg of oleum (20% of free $SO_3$) at 10°-20° C. and the mixture is stirred at room temperature for 18 hours and discharged onto ice. The crystalline precipitate is filtered off, washed with water and, if desired, dried at 60° C. in vacuo. 580 g of the compound of the formula

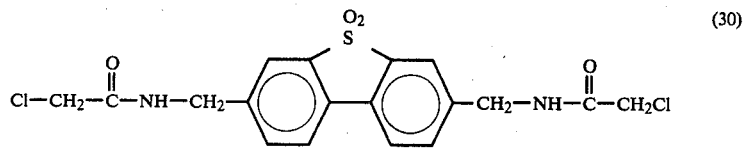

(30)

are obtained. Melting point: 287° C., with decomposition (from dimethylformamide).

$^1$H-NMR ([$D_6$]-DMSO/TMS): δ=4.23 (S; 4H, 2$CH_2Cl$), 4.50 (d, J=6 Hz; 4H, 2$CH_2$NH), 7.71 (dd, $J_1$=8 Hz, $J_2$=2 Hz; 2H), 7.88 (d, J=2 Hz; 2H), 8.17 (d, J=8 Hz; 2H), and 8.92 (t, J=6 Hz; 2H, 2$CH_2$—NH—).

If, instead of the compound (1), equal parts by weight of the compound (6) are employed, 520 g of the compound of the formula

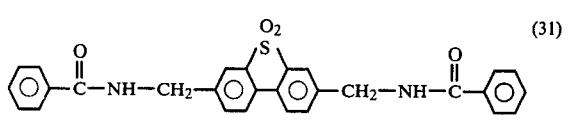

(31)

are obtained in an analogous manner. This compound is purified by boiling up with ethylene glycol monomethyl ether.

| $C_{28}H_{22}N_2SO_4$ (482.57) | calculated | C 69.69 | found | C 69.5 |
|---|---|---|---|---|
| | | H 4.60 | | H 4.8 |
| | | N 5.81 | | N 5.8 |
| | | S 6.64 | | S 6.8 |

EXAMPLE 32

50 g of the compound of the formula (30) are dissolved in 250 g of sulphuric acid (100% strength), with stirring, 250 g of oleum (65% of free $SO_3$) are added dropwise and the mixture is heated to 100° C. for 4 hours, discharged onto 1.5 kg of ice and neutralised with concentrated sodium hydroxide solution. The crystalline precipitate is filtered off over an acid-resistant filter, washed with 5% strength sodium chloride solution and dried at 50° C. in vacuo. 48 g of the compound of the

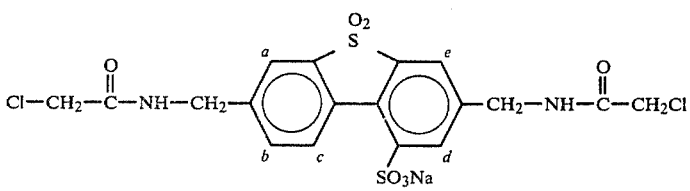

are obtained as a colourless, water-soluble crystalline powder.

$^1$H-NMR ([D$_6$]-DMSO/TMS): $\delta=4.20$ (s; 4H, 2CH$_2$Cl), 4.45 (d, J=6 Hz; 4H, 2—CH$_2$NH—), 7.66 (dd, J$_1$=9H$_z$, J$_2$=2 Hz; 1H, H$_b$), 7.79 (d, J=2H; 1H, H$_a$), AB-signal ($\delta_A=8.19$, $\delta_B=7.79$ (d, J=2 Hz; 2H, H$_d$+H$_e$), 8.92 (t, J=6 Hz; 2H, —CH$_2$—NH—), and 9.26 (d, J=9 Hz; 1H, H$_c$). $^1$H-NMR (D$_2$O/TMS): $\delta=7.70$ (dd, J$_1$=8 Hz, J$_2$=1.5 Hz; 1H, H$_b$), 7.84 (d, J=1.5 Hz; 1H, H$_a$), AB-signal ($\delta_A=8.23$, $\delta_B=7.97$, J=1.5 Hz; 2H, H$_d$+H$_e$), and 8.87 (d, J=8 Hz; 1H, H$_c$).

EXAMPLE 33

The entire amount of the moist presscake of compound (1) prepared according to Example 1 is introduced into a mixture of 1.6 l of glacial acetic acid and 1.6 l of concentrated hydrochloric acid and the mixture is warmed to 85° C. for 18 hours. After cooling to room temperature, the mixture is stirred at 20° C. for 2 hours. The crystalline precipitate is filtered off oven an acid-resistant filter and washed rapidly with 2 l of ethanol. After drying at 80° C. in vacuo, 506 g of the compound of the formula

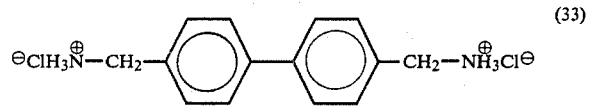

are obtained.

$^1$H-NMR (D$_2$O/TMS): $\delta=4.30$ (s; 4H), 4.82 (s; HDD in —NH$_3^{\oplus}$) and AA'BB'-signal ($\delta_A=7.85$, $\delta_B=7.60$, J$_1$=8.5 Hz, J$_2$ not resolved; 8 aromatic H). m/e (base)=212 (M$^\oplus$)

The compounds of the formulae (2) to (5) are hydrolysed in an analogous manner.

| Example | Educt | Product | m/e (base) |
|---|---|---|---|
| (34) | (2) |  | 238 (M$^\oplus$) |
| (35) | (3) | 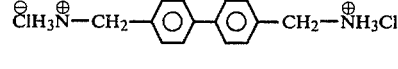 | 240 (M$^\oplus$) |

EXAMPLE 36

100 g of the compound of the formula (29) in a mixture of 400 ml of concentrated hydrochloric acid and 400 ml of glacial acetic acid are heated to the boiling point under reflux for 2 hours. The solvent is evaporated off under a waterpump vacuum. After cooling the residue to 20° C., it is stirred with 500 ml of acetone for 2 hours. The crystalline precipitate is filtered off, washed with acetone and dried at 30° C. in vacuo. 72 g of the compound of the formula

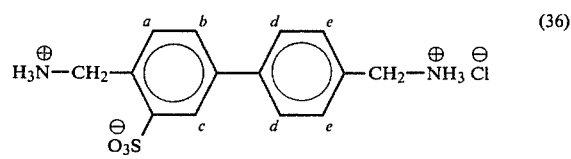

are obtained as a colourless crystalline powder which is readily water-soluble.

$^1$H-NMR ([D$_6$]-DMSO/TMS): $\delta=4.25$ (s; 2H, CH$_2$), 4.30 (s; 2H, CH$_2$), 7.33 (d, J=8 Hz; 1H, H$_a$), 7.52 (s; 4H, 2H$_d$+2H$_e$), 7.68 (dd, J$_1$=8 Hz, J$_2$=2 Hz, 1H, H$_b$), and 8.16 (d, J=2 Hz; 1H, H$_c$).

EXAMPLE 37

500 g of the compound of the formula (30) in a mixture of 2.5 l of concentrated hydrochloric acid and 2.5 l of glacial acetic acid are warmed to the boiling point under reflux for 4 hours and the mixture is then cooled. The crystalline precipitate is filtered off, washed with ethanol and dried at 50° C. in vacuo. 335 g of the compound of the formula

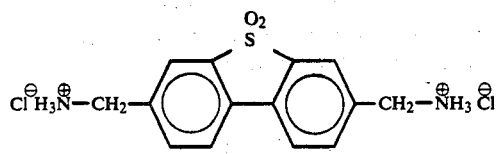 (37)

are obtained as a colourless crystalline powder which is readily water-soluble.

$^1$H-NMR ([D$_6$]-DMSO/TMS): δ=4.23 (s; 4H, 2 CH$_2$), 8.0 (dd, J$_1$=8 Hz, J$_2$=2 Hz; 2H), 8.21 (d, J not resolved; 2H), 8.28 (d, J=8 Hz; 2H), and 8.85 (s; 6H, 2NH$_3$⊕).

The compound of the formula (32) is hydrolysed in an analogous manner to give the corresponding bisaminomethyl compound of the formula

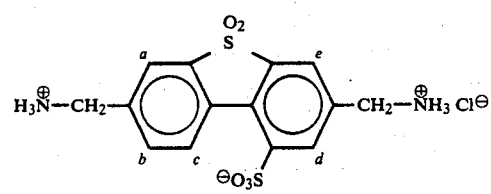 (37a)

$^1$H-NMR ([D$_6$]-DMSO/TMS): δ=4.16 (s; 2H, CH$_2$), 4.25 (s; 2H, CH$_2$), 7.92 (dd, J$_1$=8 Hz, J$_2$=1.5 Hz; 1H, H$_b$), 8.12 (d, J=1.5 Hz; 1H, H$_a$), AB-signal (δ$_A$=8.37, δ$_B$=8.16, J=2 Hz; 2H, H$_d$+H$_e$), 8.68 (broad s; 2NH$_3$⊕), and 9.35 (d, J=8 Hz; 1H, H$_c$).

EXAMPLE 38

The entire amount of the compound of the formula (18) obtained as a moist presscake in accordance with the statements of Example 18 is warmed to 85° C. in a mixture of 825 ml of glacial acetic acid and 275 ml of concentrated hydrochloric acid for 18 hours. The solvent is then evaporated off in vacuo and the residue is triturated with 500 ml of acetone.

The crystalline precipitate is filtered off, washed with acetone and dried at 50° C. in vacuo. 105 g of the compound of the formula

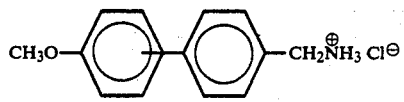 (38)

are obtained; m/e (as the base)=213.

The compounds (19), (20), (21), (22), (25), (26) and (27) are hydrolysed in an analogous manner to give the corresponding acid aminomethyl compounds.

EXAMPLE 39

142.5 g of a product of the formula (33) prepared according to Example 33 are introduced into 690 g of 100% strength sulphuric acid at 5°–15° C., whereupon hydrogen chloride escapes. The solution is stirred for 1 hour, 690 g of oleum (with 20% of free SO$_3$) are then added dropwise at 10°–20° C., with cooling, and the solution is left to stand at room temperature for 3 days and discharged onto 3 kg of ice. The crystalline precipitate is filtered off over an acid-resistant filter, washed with ice-water and dried at 80° C. in vacuo.

116 g of the compound of the formula

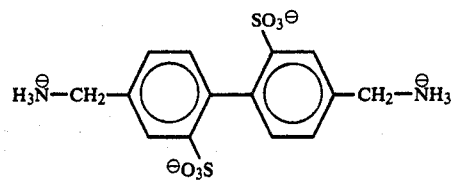 (39)

are obtained. Melting point: 327° C. (with decomposition).

$^1$H-NMR spectrum ([D$_6$]-DMSO): δ=4.28 (s; 4H, CH$_2$), 8.06 (dd, J$_1$=8.5 Hz, J$_2$=1 Hz; 2H), 8.23 (d, J=1 Hz; 2H), 8.43 (d, J=8.5 Hz; 2H) and 8.45 (broad s; 6H, —NH$_3$).

In order to disulphonate the compound from Example (34) an analogous procedure is followed, but the mixture is already worked up after standing for 20 hours (instead of 3 days) at room temperature. The compound of the formula

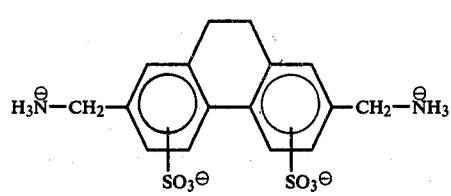 (40)

is obtained in this manner as a colourless crystalline powder which melts above 300° C., with decomposition.

EXAMPLE 41

170 g of the compound of the formula (33) are dissolved in 3.6 l of water at 85° C., and a total of 216 g of sodium nitrite is gradually added, with stirring. 240 g of concentrated hydrochloric acid are then added dropwise below the surface of the solution, still at 85° C., in the course of 1 hour. After cooling the mixture, the crystalline precipitate is filtered off, washed with water and boiled with 1 l of butyl acetate, using a water separator, in order to remove the water. After filtering off undissolved material, the solution is subjected to severe cooling. The crystalline precipitate is filtered off, washed with petroleum ether and dried at 50° in vacuo. 100.5 g of the compound of the formula

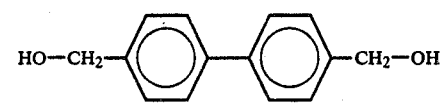 (41)

are obtained. Melting point: 188° C.; m/e=214 (M+).

EXAMPLE 42

53.5 g of the compound of the formula (41) are suspended in 200 ml of toluene, 75 g of thionyl chloride are added dropwise, with stirring, and the mixture is warmed to 40° C. for 2 hours. The solvent is then distilled off in vacuo, together with the excess thionyl chloride. 63 g of the compound of the formula

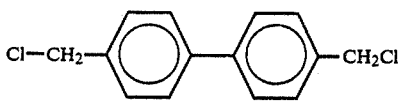
(42)

are obtained as the residue; m/e=250 (M⊕, dichloro). The compound is further processed without intermediate isolation:

(A) In accordance with the statements of German Auslegeschrift No. 1,794,386, column 18, 4,4'-bis-(chloromethyl)-biphenyl (42) is converted into 4,4'-bis-(dimethoxy-phosphonomethyl)-biphenyl by reaction with trimethyl phosphite and this product is subjected to a condensation reaction with benzaldehyde-2-sulphonic acid to give 4,4'-bis-(2-sulphostyryl)-biphenyl, which is an optical brightener which can be applied to cotton and polyamide from wash liquors.

(B) In accordance with the statements of German Offenlegungsschrift No. 2,238,734, 4,4'-bis-(chloromethyl)biphenyl (42) is reacted with salicylaldehyde to give 4,4'-bis-(benzo[b]furan-2-yl)-biphenyl and this product is reacted further with oleum to give a mixture of the corresponding tri- and tetra-sulphonic acids. This mixture can also be used for the optical brightening of cotton and polyamide.

EXAMPLE 43

150 g of the compound of the formula (6) are suspended in 900 ml of o-dichlorobenzene, 164.3 g of phosphorus pentachloride are added and the mixture is heated to 110°–115° C. for 1.5 hours, some of the POCl₃ formed being allowed to distil off. The remainder of the POCl₃ is then distilled off under a waterpump vacuum, together with the solvent and the benzonitrile formed (a bath temperature of up to 130° C.). The residue (98 g) is recrystallised from 450 ml of methylcyclohexane. 78 g of the compound of the formula (42) are obtained.

A similar result is obtained if, instead of PCl₅, 115 ml of thionyl chloride are employed, the mixture is heated to 80° C. for 1.5 hours, the excess SOCl₂ is distilled off, the mixture is heated for a further 10 hours to 150° C., the solvent and benzonitrile are distilled off in vacuo and the residue is recrystallized as described above.

If compound (6) is replaced by one of the compounds of the formulae (7) to (15), 4,4'-(bischloromethyl)-biphenyl (42) is in each case obtained in a similarly high yield in an analogous manner.

Example 44

70 ml of 30% strength NaCN solution are added to 50.2 g of the compound of the formula (42) in 400 ml of dimethylformamide at 40° C. and the mixture is stirred at 40–45° C. for 2 hours. After discharging the mixture onto 2 l of ice-water, the crystalline precipitate is filtered off, washed with water and dried at 50° C. in vacuo. 38 g of the compound of the formula

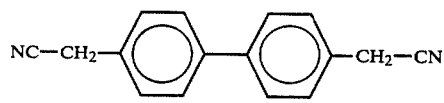
(44)

of melting point 168° C. are obtained; m/e=232 (M⊕).

EXAMPLE 45

373 g of the compound of the formula (33), as a moist presscake (700 g), and 730 g of urotropin in a mixture of 1.3 l of glacial acetic acid and 1.3 l of water are heated to the boiling point under reflux for 2 hours and the mixture is cooled. The crystalline precipitate is filtered off, washed with water and dried at 50° C. in vacuo. 252 g of the compound of the formula

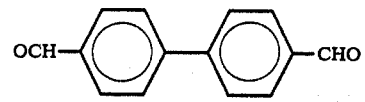
(45)

are obtained as a colourless crystalline powder. Melting point: 139° C. (from di-n-butyl ether), m/e=210 (M⊕).

The mother liquor can advantageously be re-used for subsequent batches, it being necessary to employ in each case only half the amount of urotropin originally used. Valuable optical brighteners of the 4,4'-distyryl-biphenyl series can be prepared from (45) in accordance with German Auslegeschrift No. 1,794,386, German Offenlegungsschrift No. 2,241,304 and German Offenlegungsschrift No. 3,001,876, and valuable dyestuffs for paper can be prepared in accordance with German Offenlegungsschrift No. 2,901,845.

From the compounds (34) and (35), the corresponding dialdehydes of the formulae

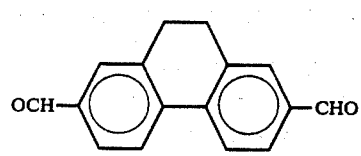
(46)

(m/e = 238, M⊕) and

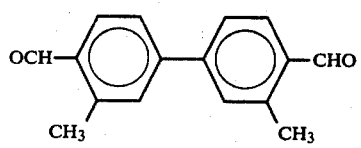
(47)

(m/e = 240, M⊕)

are prepared in an analogous manner.

EXAMPLE 48

300 g of the compound of the formula (37) and 250 g of urotropin in 1.5 kg of glacial acetic acid and 70 ml of water are heated to the boiling point under reflux for 3 hours and the mixture is cooled. The resulting precipitate is filtered off, washed with methanol and dried at 50° C. in vacuo. 153 g of the compound of the formula

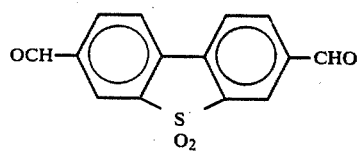
(48)

are obtained as a colourless crystalline powder. Melting point: 302° C.; m/e=272 (M⊕) (from dimethylformamide).

EXAMPLE 49

In an analogous manner, but without the treatment with sulphuric acid, compound (37a) is converted into the dialdehyde of the formula

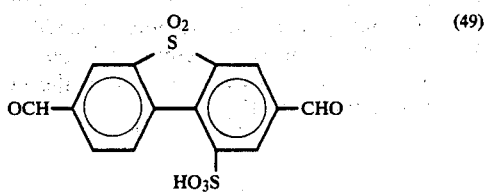
(49)

which, after precipitation with isopropanol, is isolated.

EXAMPLE 50

6.6 g of the compound of the formula (36) and 5.6 g of urotropin in 90 ml of glacial acetic acid are heated to the boiling point under reflux for 3 hours, the mixture is cooled to 30° C., 6.2 g of p-nitrophenylhydrazine are added and the mixture is stirred at 30°–40° C. for 30 minutes and cooled to 20° C. The crystalline precipitate is filtered off, washed with methanol and dried at 40° C. in vacuo. 8.8 g of the compound of the formula

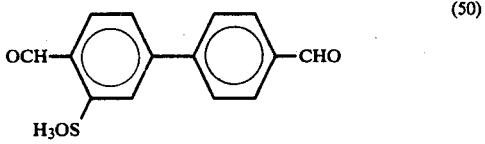
(50)

are obtained as the bis-p-nitrophenylhydrazone (orange-coloured crystalline powder, melting point: 300° C.).

EXAMPLE 51

200 g of the compound of the formula (1) are introduced into 1 kg of oleum (20% of free $SO_3$) at room temperature, with cooling and stirring, and the mixture is stirred at room temperature for 18 hours, whereupon the compound of the formula (30) is formed. This compound is hydrolysed, without intermediate isolation, to give the compound of the formula (37), in this case with 2 $HSO_4^\oplus$ instead of with 2 $Cl^\oplus$. For this hydrolysis, a procedure is followed in which 430 ml of water are added dropwise, with severe cooling and with stirring, and the mixture is warmed to 100° C. for 8 hours and cooled. The crystalline precipitate is filtered off, washed with 600 ml of 8% strength sodium chloride solution and dried at 60° C. in vacuo. 128 g of the compound of the formula (37) are obtained as the 2 $HSO_4^\oplus$ salt.

EXAMPLE 52

200 g of the compound of the formula (1) are introduced into 1 kg of oleum (20% of free $SO_3$) at room temperature, with cooling and stirring, and the mixture is stirred at room temperature for 18 hours, whereupon the compound of the formula (30) is formed. This compound is sulphonated, without intermediate isolation, to give the compound of the formula (32) (free sulphonic acid instead of the Na salt) and the product is then hydrolysed, without intermediate isolation, to give the compound (37a) ($HSO_4^\oplus$ salt). For this hydrolysis, a procedure is followed in which 1 kg of oleum (65% of free $SO_3$ is added dropwise and the mixture is warmed to 80° C. for 6 hours, diluted with 1.6 liters of water, with cooling and with stirring, heated to 100° C. for 8 hours and cooled. The crystalline precipitate is filtered off, washed with 600 ml of 8% strength sodium chloride solution and dried at 60° C. in vacuo. 136 g of the compound of the formula (37a) are obtained as the $HSO_4^\oplus$ salt.

I claim:

1. Compounds of the formula

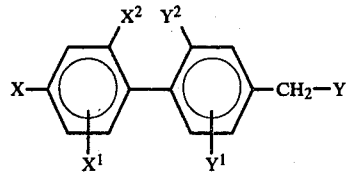

wherein

X represents hydrogen, —$CH_2$—Y, $SO_3H$ or a radical A,

A represents $C_1$–$C_6$-alkyl, trifluoromethyl, cyclohexyl, $C_1$–$C_4$-alkoxy, chlorine, bromine or fluorine, $X^1$ represents hydrogen, methyl, chlorine or $SO_3H$, $X^2$ represents hydrogen or methyl, Y represents an acetamido or propionylamido radical which is substituted in the α-position by 1 to 3 halogen atoms, or a phthalimido group, or a benzamido group optionally substituted on the nucleus by up to three $C_1$–$C_4$-alkyl, chlorine, bromine, methoxy, ethoxy, nitro and/or cyano groups and or at the amido nitrogen atom by a $C_1$–$C_2$-alkyl group, $Y^1$ represents hydrogen, methyl or $SO_3H$ and $Y^2$ represents hydrogen, or $X^2$ and $Y^2$ together form an ethylene radical or a —$SO_2$— bridge, with the proviso that at least one radical Y represents halogen-substituted acetamido or propionylamido or optionally substituted benzamido if the compounds are free from sulphonic acid groups or from —$SO_2$— bridges.

2. Compounds of the formula

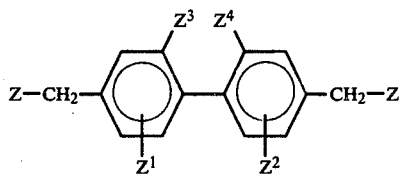

wherein

Z represents chloroacetamido, dichloroacetamido, trichloroacetamido or benzamido, $Z^1$ and $Z^2$ independently of one another represent hydrogen or $SO_3H$ and $Z^3$ and $Z^4$ individually represent hydrogen or together represent ethylene or a —$SO_2$— bridge.

3. Compounds of the formula

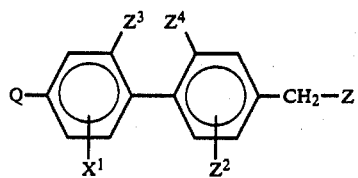

wherein

Z represents chloroacetamido, dichloroacetamido, trichloroacetamido or benzamido, $Z^2$ represents hydrogen or $SO_3H$, $Z^3$ and $Z^4$ individually represent hydrogen or together represent ethylene or a $-SO_2-$ bridge, Q represents hydrogen, $C_1-C_4$-alkyl, cyclohexyl, $C_1-C_2$-alkoxy, chlorine, bromine or $SO_3H$ and $X^1$ represents hydrogen, methyl, chlorine or $SO_3H$, with the proviso that at most one of the radicals Q and $X^1$ denotes $SO_3H$.

* * * * *

UNITED STATES PATENT AND TRADEMARK OFFICE
CERTIFICATE OF CORRECTION

PATENT NO. : 4,370,486

Page 1 of 2

DATED : January 25, 1983

INVENTOR(S) : Horst Harnisch

It is certified that error appears in the above-identified patent and that said Letters Patent is hereby corrected as shown below:

Columns 15 and 16 should be added as part of Letters Patent as shown on the attached sheet.

Signed and Sealed this

Eleventh Day of September 1984

[SEAL]

Attest:

GERALD J. MOSSINGHOFF

Attesting Officer

Commissioner of Patents and Trademarks are obtained in an analogous manner. This compound is purified by boiling up with ethylene glycol monomethyl ether.

| $C_{28}H_{22}N_2SO_4$ (482.57) | calculated | C 69.69 | found | C 69.5 |
|---|---|---|---|---|
| | | H 4.60 | | H 4.8 |
| | | N 5.81 | | N 5.8 |
| | | S 6.64 | | S 6.8 |

EXAMPLE 32

50 g of the compound of the formula (30) are dissolved in 250 g of sulphuric acid (100% strength), with stirring, 250 g of oleum (65% of free $SO_3$) are added dropwise and the mixture is heated to 100° C. for 4 hours, discharged onto 1.5 kg of ice and neutralised with concentrated sodium hydroxide solution. The crystalline precipitate is filtered off over an acid-resistant filter, washed with 5% strength sodium chloride solution and dried at 50° C. in vacuo. 48 g of the compound of the

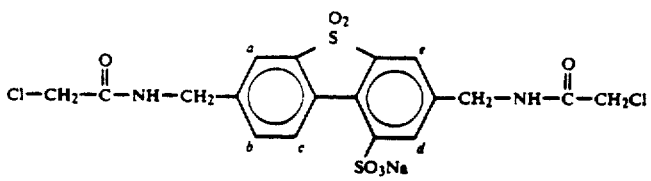
(32)

are obtained as a colourless, water-soluble crystalline powder.

$^1$H-NMR ([D$_6$]-DMSO/TMS): δ=4.20 (s; 4H, 2CH$_2$Cl), 4.45 (d, J=6 Hz; 4H, 2—CH$_2$NH—), 7.66 (dd, J$_1$=9H$_z$, J$_2$=2 Hz; 1H, H$_b$), 7.79 (d, J=2H; 1H, H$_a$), AB-signal (δ$_A$=8.19, δ$_B$=7.79 (d, J=2 Hz; 2H, H$_d$+H$_e$), 8.92 (t, J=6 Hz; 2H, —CH$_2$—N<u>H</u>—), and 9.26 (d, J=9 Hz; 1H, H$_c$). $^1$H-NMR (D$_2$O/TMS): δ=7.70 (dd, J$_1$=8 Hz, J$_2$=1.5 Hz; 1H, H$_b$), 7.84 (d, J=1.5 Hz; 1H, H$_a$), AB-signal (δ$_A$=8.23, δ$_B$=7.97, J=1.5 Hz; 2H, H$_d$+H$_e$), and 8.87 (d, J=8 Hz; 1H, H$_c$).

EXAMPLE 33

The entire amount of the moist presscake of compound (1) prepared according to Example 1 is introduced into a mixture of 1.6 l of glacial acetic acid and 1.6 l of concentrated hydrochloric acid and the mixture is warmed to 85° C. for 18 hours. After cooling to room temperature, the mixture is stirred at 20° C. for 2 hours. The crystalline precipitate is filtered off oven an acid-resistant filter and washed rapidly with 2 l of ethanol. After drying at 80° C. in vacuo, 506 g of the compound of the formula

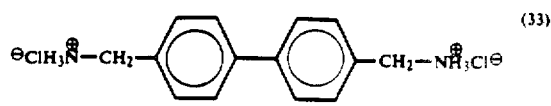
(33)

are obtained.

$^1$H-NMR (D$_2$O/TMS): δ=4.30 (s; 4H), 4.82 (s; HDD in —NH$_3^⊕$) and AA'BB'-signal (δ$_A$=7.85, δ$_B$=7.60, J$_1$=8.5 Hz, J$_2$ not resolved; 8 aromatic H). m/e (base)=212 (M$^⊕$)

The compounds of the formulae (2) to (5) are hydrolysed in an analogous manner.

| Example | Educt | Product | m/e (base) |
|---|---|---|---|
| (34) | (2) | ⊖ClH$_3$N$^⊕$—CH$_2$—[naphthyl]—CH$_2$—N$^⊕$H$_3$Cl⊖ | 238 (M$^⊕$) |
| (35) | (3) | ⊖ClH$_3$N$^⊕$—CH$_2$—[Ar(CH$_3$)—Ar(CH$_3$)]—CH$_2$—N$^⊕$H$_3$Cl⊖ | 240 (M$^⊕$) |

EXAMPLE 36

100 g of the compound of the formula (29) in a mixture of 400 ml of concentrated hydrochloric acid and 400 ml of glacial acetic acid are heated to the boiling point under reflux for 2 hours. The solvent is evaporated off under a waterpump vacuum. After cooling the residue to 20° C., it is stirred with 500 ml of acetone for 2 hours. The crystalline precipitate is filtered off, washed with acetone and dried at 30° C. in vacuo. 72 g of the compound of the formula

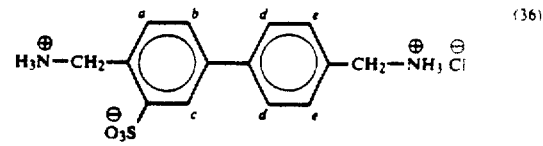
(36)

are obtained as a colourless crystalline powder which is readily water-soluble.

$^1$H-NMR ([D$_6$]-DMSO/TMS): δ=4.25 (s; 2H, CH$_2$), 4.30 (s; 2H, CH$_2$), 7.33 (d, J=8 Hz; 1H, H$_a$), 7.52 (s; 4H, 2H$_d$+2H$_e$), 7.68 (dd, J$_1$=8 Hz, J$_2$=2 Hz; 1H, H$_b$), and 8.16 (d, J=2 Hz; 1H, H$_c$).

EXAMPLE 37

500 g of the compound of the formula (30) in a mixture of 2.5 l of concentrated hydrochloric acid and 2.5 l of glacial acetic acid are warmed to the boiling point under reflux for 4 hours and the mixture is then cooled. The crystalline precipitate is filtered off, washed with